US009039697B2

(12) United States Patent
Lischinsky et al.

(10) Patent No.: US 9,039,697 B2
(45) Date of Patent: May 26, 2015

(54) ELECTROSURGICAL METHODS AND DEVICES EMPLOYING INDUCTIVE ENERGY

(75) Inventors: Daniel Lischinsky, Ramat Yishai (IL); Yoram Harth, Herzliya (IL)

(73) Assignee: EndyMed Medical Ltd., Caesarea (IL)

( * ) Notice: Subject to any disclaimer, the term of this patent is extended or adjusted under 35 U.S.C. 154(b) by 1488 days.

(21) Appl. No.: 12/673,878

(22) PCT Filed: Aug. 18, 2008

(86) PCT No.: PCT/IB2008/003000
§ 371 (c)(1),
(2), (4) Date: Jan. 25, 2011

(87) PCT Pub. No.: WO2009/047628
PCT Pub. Date: Apr. 16, 2009

(65) Prior Publication Data
US 2011/0118722 A1    May 19, 2011

Related U.S. Application Data

(60) Provisional application No. 60/956,497, filed on Aug. 17, 2007.

(51) Int. Cl.
| A61B 18/14 | (2006.01) |
| A61B 18/12 | (2006.01) |
| A61N 1/06 | (2006.01) |
| A61B 18/00 | (2006.01) |
| A61N 2/00 | (2006.01) |

(52) U.S. Cl.
CPC ....... *A61B 18/12* (2013.01); *A61B 2018/00577* (2013.01); *A61B 2018/00738* (2013.01); *A61B 2018/1467* (2013.01); *A61N 1/06* (2013.01); *A61N 2/002* (2013.01)

(58) Field of Classification Search
USPC ...................................... 606/32–50
See application file for complete search history.

(56) References Cited

U.S. PATENT DOCUMENTS

| 6,711,435 | B2 | 3/2004 | Avrahami | |
| 6,892,099 | B2* | 5/2005 | Jaafar et al. | 607/72 |
| 2004/0231683 | A1 | 11/2004 | Eng et al. | |
| 2005/0187545 | A1 | 8/2005 | Hooven et al. | |
| 2007/0083075 | A1 | 4/2007 | Ein-Gal | |
| 2007/0088347 | A1* | 4/2007 | Young et al. | 606/41 |
| 2007/0191827 | A1 | 8/2007 | Lischinsky et al. | |

FOREIGN PATENT DOCUMENTS

| DE | 102007061767 A1 | 12/2008 |
| WO | WO-0044437 A1 | 8/2000 |
| WO | WO-2007047239 A2 | 4/2007 |

OTHER PUBLICATIONS

International Search Report for PCT Application No. PCT/IB2008/003000 date of mailing Jul. 20, 2009 (4 pgs.).

* cited by examiner

*Primary Examiner* — Michael Peffley
(74) *Attorney, Agent, or Firm* — Pearl Cohen Zedek Latzer Baratz LLP

(57) ABSTRACT

This disclosure relates generally to methods and devices for modifying biological tissue. In one embodiment, a device is provided suitable for applying RF energy to a treatment site in the presence of a supplemental magnetic field. The device comprises one or more electrodes electrically coupled to an RF generator, and a means for supplying a supplemental magnetic field. In another embodiment, a device is provided suitable for inducing an electrical current in a tissue. The device comprises a means for creating a magnetic field and a passive element adapted for reducing the amount of electrical current at the surface of the tissue. Also provided are methods of use of such devices. The methods and devices disclosed herein find utility, for example, in the field of medicine and cosmetology.

18 Claims, 18 Drawing Sheets

• = Head of Magnetic line
⊙ = Tail of Magnetic line

• = Head of Magnetic line
◉ = Tail of Magnetic line

Side (Z,Y)

• = Head of Magnetic line
⊙ = Tail of Magnetic line
- - -▶ = Electrical current path Side (Z,Y)

ELECTROSURGICAL METHODS AND DEVICES EMPLOYING INDUCTIVE ENERGY

RELATED APPLICATIONS

This application is a national stage application, filed under 35 U.S.C. §371, of International Application No. PCT/IB2008/003000, filed on Aug. 18, 2008, which claims the benefit of U.S. Patent Application Ser. No. 60/956,497, filed on Aug. 17, 2007.

TECHNICAL FIELD

This disclosure relates generally to electrosurgical methods and devices suitable for treating tissue with electromagnetic energy. The invention finds utility, for example, in the fields of medicine and cosmetology.

BACKGROUND

Radiofrequency (RF) devices are used to ablate or heat different types of tissue. For example, in the field of dermatology RF devices are used to treat aging skin. Skin aging is associated with changes in the upper levels of the skin such as roughness of the skin due to changes in the stratum corneum and epidermis and uneven pigmentation in the epidermis. In the dermis, aging and environmental factors cause the destruction and malfunction of collagen and elastin fibers leading to the formation of wrinkles. Symptoms of skin aging in the epidermis are typically treated by ablative methods such as chemical peels or laser resurfacing. Optical radiation devices such as lasers are used to resurface large areas of the skin. While these lasers are effective in the treatment of the signs of skin aging, resurfacing the whole epidermis is often associated with side effects such as wound infections, prolonged healing times, hyperpigmentation, hypopigmentation, and scarring.

Radiofrequency devices are used to ablate localized skin lesions or to destroy the whole upper surface of the skin. However, whole skin resurfacing methods and devices cause burn-like post treatment reactions that may be associated with prolonged healing times, increased risk of infections, prolonged erythema, scarring, hyperpigmentation, and hypopigmentation.

U.S. Pat. No. 6,711,435 discloses a device for ablating the stratum corneum epidermis of a subject, including a plurality of electrodes, which are applied to the subject's skin at respective points. However, this device does not ablate the epidermis or dermis and thus has no effects on the signs of skin aging.

Symptoms of skin aging in the dermis are typically treated by non-ablative methods, including lasers, intense pulsed light, or RF devices that heat the dermis to trigger renewal of collagen fibers. In order to trigger collagen renewal, some RF devices use bipolar electrodes to increase the heat of dermal skin layers through the creation of electrical currents that flow parallel to the skin surface. These devices use active and return electrodes that are typically positioned relatively close to one another at the treatment site. In some cases, the two electrodes are located on the same electrosurgical probe, and the electrodes alternate between functioning as active and return electrodes. Typically, for bipolar devices, electrical currents created in the target tissue create a density gradient in which the upper layers of tissue (i.e., those layers of tissue nearer to the electrodes) carry more current, while the lower layers of tissue (i.e., those layers of tissue farther from the electrodes) carry less current. Therefore, electrical current density varies inversely as a function of depth below the surface of the tissue being treated. Other RF devices use unipolar or monopolar electrical energy for heating the deep layers of skin. These devices also use an active electrode and a return electrode. The return electrode is typically positioned a relatively large distance from the active electrode (in comparison with bipolar devices). For both unipolar and bipolar devices, current flows along the lowest impedance path between electrodes.

The devices described previously lack the ability to control the spatial directions, energies, and/or nature of the electrical energies affecting the treated area and thus lack the selectivity and specificity needed for maximum efficacy in their respective therapeutic indications. Moreover, the non-ablative bipolar and monopolar RF devices lack the ability to treat the signs of aging in the epidermis. Enhanced ability to control the spatial directions and the pattern of electron flows in the treated biological tissue would allow effective therapy for additional dermatological and non-dermatological disorders such as hair removal, acne, acne scars, cellulite, psoriasis, bone grafting and more.

Despite advancements in the use of RF devices for treating biological tissue, therefore, there continues to be a need in the art to develop effective ablative and non-ablative electrosurgical devices and methods that are suitable for treating a wide variety of conditions. An ideal electrosurgical method and related devices would be capable of selectively and specifically treating a wide variety of biological tissues and conditions affecting such tissues. Such a method and the associated devices would be simple to use, and would have minimal adverse effects.

SUMMARY OF THE DISCLOSURE

The present disclosure is directed at addressing one or more of the abovementioned drawbacks of known electrosurgical methods and devices.

In one embodiment, then, the disclosure provides a method for treating a biological tissue having a surface. The method comprises applying to the tissue an electromagnetic field and modifying the electromagnetic field with a supplemental magnetic field. The electromagnetic field is generated by providing RF power to one or more primary electrodes and is effective to create an electrical current in the tissue at a first depth below the surface and an electrical current in the tissue at a second depth below the surface.

In another embodiment, the disclosure provides a device for applying RF energy to biological tissue. The device comprises one or more primary electrodes disposed on a treatment probe. The device also comprises a means for supplying RF energy to the one or more primary electrodes. The device further comprises a means for creating a supplemental magnetic field.

In yet another embodiment, the disclosure provides a method for inducing an electrical current in a tissue. The method comprises applying a magnetic field to the tissue and contacting a surface of the tissue with a passive element having a resistivity that is less than the resistivity of the tissue.

In another embodiment, the disclosure provides a device for inducing an electrical current in a biological tissue. The device comprises a means for creating a magnetic field and a passive element adapted to contact the tissue and provide a path of low electrical resistance between two locations on the tissue.

DETAILED DESCRIPTION OF THE INVENTION

Figure 1A:
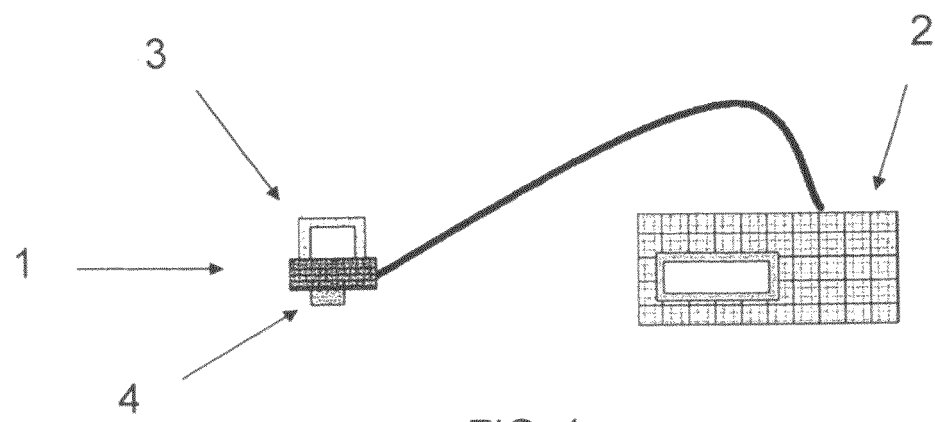
FIGS. 1a and 1b are example illustrations of electrosurgical probes as disclosed herein.

Before describing the present invention in detail, it is to be understood that unless otherwise indicated, this invention is not limited to particular electrosurgical methods, electrosurgical devices, or power sources, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, "a power source" refers not only to a single power source but also to a combination of two or more power sources, "an electrode" refers to a combination of electrodes as well as to a single electrode, and the like.

Unless defined otherwise, all technical and scientific terms used herein have the meaning commonly understood by one of ordinary skill in the art to which the invention pertains. Although any methods and materials similar or equivalent to those described herein may be useful in the practice or testing of the present invention, preferred methods and materials are described below. Specific terminology of particular importance to the description in the present disclosure is defined below.

As used herein, the terms "may," "optional," "optionally," or "may optionally" mean that the subsequently described circumstance may or may not occur, so that the description includes instances where the circumstance occurs and instances where it does not.

The term "electrosurgical" is used herein to refer to devices and methods that modify biological tissue. Unless otherwise specified, the term is not limited to any particular type of modification.

As used herein, the term "device" is meant to refer to any and all components of a system. For example, an "electrosurgical device" refers to an electrosurgical system that may comprise components such as electrosurgical probes, power sources, connecting cables, and other components.

The terms "treating" and "treatment" as used herein refer to reduction in severity and/or frequency of symptoms, elimination of symptoms and/or underlying cause, prevention of the occurrence of symptoms and/or their underlying cause (e.g., prophylactic therapy), and improvement or remediation of damage.

By "patient," or "subject" is meant any animal for which treatment is desirable. Patients may be mammals, and typically, as used herein, a patient is a human individual.

The terms "user" or "practitioner" as used herein refer to individuals that may use the devices and methods of the disclosure in order to treat a patient.

Unless otherwise specified, the terms "treatment site," "target site," "target tissue" and "target" are used interchangeably and refer to the portion of the patient that is in need of treatment or is receiving treatment. The target tissue generally includes layers of tissue that are altered by the methods of the disclosure, and may include one or more layers of surrounding tissue. The target tissue may be isolated or may be part of a larger organ, such as in the case of the epidermis or dermis of skin (i.e., epidermis or dermis is the target tissue and skin is the organ).

The terms "light" and "light energy" as used herein are meant to include visible, infrared, and ultraviolet electromagnetic energy.

It will be appreciated that many biological tissues comprise a plurality of layers. For example, skin comprises the stratum corneum, epidermis, dermis, and hypodermis (listed in order of increasing depth below the surface). As used herein and unless otherwise specified, the term "surface" (as in the "surface" of a tissue) is used to indicate the top or exposed portion of the outermost layer of a tissue. The term "surface layers" (as in the "surface layers" of a tissue) generally refers to the outermost layer as well as a number of underlying layers of cells forming the tissue. The number of underlying layers of cells that is included when reference to "surface layers" will vary according to the specific reference, but will typically include between 1 and 1000 layers (or more) of cells. For example, "surface layers" may include between 1 and 500 layers, as a further example between 1 and 100 layers, as a further example between 1 and 10 layers, or for example between 1 and 5 layers.

In one embodiment, then, there is disclosed herein electrosurgical devices for applying RF energy to a treatment site. Preferred treatment sites are biological tissue such as the skin of a patient. In preferred embodiments, the devices of the disclosure modulate spatially the flow of electrical current and heat in the tissue. Also disclosed herein are procedures for using the electrosurgical devices to treat a variety of conditions.

An electrosurgical device according to the disclosure comprises a means for creating an electrical current in the target tissue. In preferred embodiments, the means for creating an electrical current in the target tissue comprises one or more primary electrodes. The primary electrodes may be disposed on a probe, such as on the treatment surface of an electrosurgical probe. The primary electrodes are configured such that, when the treatment surface is applied to the target tissue, the primary electrodes make physical and/or electrical contact with the target tissue. Application of a primary voltage across the primary electrodes creates an electromagnetic field (also referred to herein as a "primary electromagnetic field") that, when applied to the target tissue, causes the formation of a primary electrical current through the target tissue. The primary voltage is preferably supplied by a primary power source which is described in detail below. Associated with the primary electrical current is a primary magnetic field according to the laws of electromagnetism.

The electrosurgical probes of the disclosure further comprise a means for supplying a supplemental magnetic field. As used herein, and unless otherwise specified, the term "supplemental magnetic field" is synonymous and interchangeable with "cooling magnetic field," and "external magnetic field." The means for supplying a supplemental magnetic field is configured such that the supplemental magnetic field can interact with the electromagnetic field created by the primary electrodes to influence the path, current density, and/or other characteristics of the primary electrical current.

Generally, the means for supplying a supplemental magnetic field comprises one or more supplemental electrodes such as one or more inductors. In preferred embodiments, the means for supplying a supplemental magnetic field comprises one or more supplemental wires electrically coupled to a supplemental power source such that the wire may carry a supplemental electrical current. Other embodiments of the means for supplying a supplemental magnetic field will be apparent to the skilled artisan, and include embodiments such as a conducting coil or plurality of coils, a spiral (e.g., on a printed circuit board), or any other type of inductor. It will be appreciated that inductors in the form of coils may be wound around any appropriate material (including bobbins made of ferromagnetic material such as ferrite), or may have no core material other than air. Furthermore, the means for supplying a supplemental magnetic field may be located on the electrosurgical probe, or it may be separate from the electrosurgical probe (such as on a supplemental electrosurgical probe).

In another embodiment, the means for supplying a supplemental magnetic field comprises a permanent magnet (e.g., a body of ferromagnetic material).

In preferred embodiments, the supplemental electrode is located on or near the treatment surface of the electrosurgical probe. In some embodiments, the supplemental electrode extends across all or a portion of the space that is spanned by the primary electrodes, although it will be appreciated that the supplemental electrode must be insulated from the primary electrodes. Furthermore, the supplemental electrode must be insulated or positioned such that it does not electrically contact the target tissue during normal operation of the electrosurgical device. Such insulation may be accomplished, for example, by embedding the supplemental electrode within (wholly or partially) the treatment portion of the electrosurgical probe.

The primary power source is typically an RF generator capable of supplying one or more RF signals. The primary power source may supply RF signals having a frequency of at least 850 kHz, or at least 1 MHz, or at least 1.2 MHz. The primary power source will generally be capable of supplying a sufficient amount of power to create an electrical current in biological tissue and thereby raise the temperature of the tissue. In preferred embodiments, such temperature increase will be sufficient to cause a modification of the tissue. For example, the temperature increase may be sufficient to cause contraction of collagen, or sufficient to cause desiccation of tissue, or sufficient to cause ablation of tissue, or sufficient to cause charring of tissue.

In some embodiments, the amount of power supplied to the tissue via the primary electrodes will be at least 5 watts, or at least 25 watts, or at least 50 watts, or at least 60 watts.

The supplemental power source may be the same as the primary power source (i.e., the primary power source supplies power to the primary electrodes and the supplemental wire), or, alternatively, the supplemental power source may be different from the primary power source. The supplemental power source may provide either a direct current (DC) or an alternating current (AC) signal. When the supplemental power source delivers an AC signal to the supplemental electrode, the frequency of the AC signal may be any appropriate frequency. In preferred embodiments, the frequency of the AC signal will be an integer multiple of the frequency of the RF signal supplied by the primary power source. For example, the frequency of the AC signal may be 1×, 2×, 3×, 4×, etc., where "x" is the frequency of the RF signal supplied by the primary power source.

The polarity of the connection between the supplemental electrode and the supplemental power source may be selected to obtain the desired effect. For example, the supplemental electrode may be connected to the supplemental power source such that the supplemental electrical current flows in the direction that is opposite that of the primary electrical current or the polarity may be such that the primary and supplemental electrical currents flow in the same direction. It will be appreciated that the polarity of the supplemental power source may be selected by the user, such selection being based on the application for which the electrosurgical device is being used. In some preferred embodiments, the polarity of the supplemental power source can be modified (e.g., reversed) as needed before or during operation of the electrosurgical device to obtain a desirable effect. Modification of the polarity of the connection between the supplemental power source and the supplemental wire may be carried out by any suitable means, such as a controlling switch on the supplemental power supply or on the electrosurgical probe.

Electrical power may be supplied to the electrosurgical probe at any time before or during treatment. For example, power may be supplied prior to applying the treatment surface of the electrosurgical probe to the target tissue. Alternatively, power may be supplied after the treatment surface has been placed in position and is ready to treat the target tissue. Power may be supplied to and/or removed from the primary electrodes and the supplemental electrode at the same time, or at different times. In a preferred embodiment, power is applied and removed simultaneously to the supplemental electrode and the primary electrodes. The electrosurgical devices of the disclosure may also comprise a means for interrupting one or both of the primary electrical current and the supplemental electrical current. Such means may be, for example, a switch on the primary power supply and/or a switch on the supplementary power supply (when present). Therefore, devices wherein the power supplied to the primary electrodes and the power supplied to the supplementary wire are independently controlled are within the scope of the disclosure.

It will be appreciated that, although references are made herein to a plurality of primary electrodes and a single supplemental electrode, such references are not meant to be limiting, and the disclosure also includes embodiments having a single primary electrode and/or a plurality of supplemental electrodes.

The primary electrodes may be of any appropriate size or shape, and it will be appreciated that such will vary depending, for example, on the intended use. The treatment surface can be adapted to treat a variety of biological tissues. Accordingly, the treatment surface may be flat or curved. For devices with more than two primary electrodes, the electrodes may be uniformly disposed across the entire treatment surface, or may be concentrated in a particular section of the treatment surface. Typically, a regular pattern will be formed by the distribution of the electrodes on the treatment surface.

The electrosurgical probes of the disclosure comprise at least one primary electrode, and in preferred embodiments will comprise two or more primary electrodes. For example, the probes may comprise any number of primary electrodes such as 2, 3, 4, 5, 6, 7, 8, 9, 10, 15, 20, 50, 100, or more. Each primary electrode or pair of primary electrodes may be associated with a supplemental electrode, or a single supplemental electrode may be present that interacts with the magnetic fields produced by one or all of the pairs of primary electrodes.

The primary electrodes may be arranged in any appropriate manner on the treatment surface. For example, the primary electrodes may have a circular cross-section and be disposed in a regular pattern over a flat treatment surface. The primary electrodes may be either flush with the treatment surface, or the primary electrodes may protrude from the treatment surface.

The spacing between electrodes will depend, for example, on the probe geometry, the size and number of electrodes, and other factors that will be appreciated by the skilled artisan. In general, the spacing between the centers of any two adjacent electrodes will be between about 110% and about 1000% of the diameter of the electrodes, or, for non-circular electrodes, the spacing will be between about 110% and about 1000% of the maximum width of the electrodes. For treatment of human skin, for example, the center-to-center distance between adjacent electrodes may be between about 0.001 mm and about 100 mm, or between about 0.01 mm and about 25 mm. In one embodiment, adjacent electrodes are spaced apart an average of about 0.01 mm to about 1.0 cm.

A handle portion insulates the user of the device from the treatment portion and the electrodes, and should be adapted to promote maneuvering and manipulation of the treatment portion. The electrosurgical probe and components thereof are not limited to any particular shape, material, size, etc., as long as they serve the functions described herein.

The electrosurgical probe is electrically coupled to the power supply using any appropriate arrangement. For example, the primary electrodes may be connected to wires that run the length of the handle portion, exit at the distal end of the handle portion, and attach to or connect to the power supply. Additional components such as controlling devices may also be connected in parallel or in series with the power supply and the electrosurgical probe. Any appropriate power supply may be used, particularly preferred are those power supplies that are commonly used in electrosurgical devices. The power supply may be dedicated to and/or integrated with the electrosurgical probe, or a general power supply (such as those commonly found in medical treatment facilities) may be used.

The electrosurgical devices described herein are useful in methods for delivering energy to a target site of a patient. Target sites suitable for the application of electrical energy using the devices disclosed herein include biological tissues such as skin, mucous membranes, organs, blood vessels, and the like. Energy is delivered to the target tissue via an electrosurgical probe, which is placed in close proximity to the target site. By "close proximity" is meant that the probe is placed close enough to the target site to have a desired effect (e.g., tissue ablation, warming of the target site, etc.). In preferred embodiments, the electrosurgical probe is placed in contact with a portion of the target site. For example, when the target tissue is skin, the electrosurgical probe is place in contact with the outermost layer of skin.

With the electrosurgical probe in close proximity to the target site, an RF electrical potential is applied across the primary electrodes present on the electrosurgical probe. This potential will cause a primary electrical current to flow within the target site and between the electrodes. Where only a single primary electrode is used, a return electrode (typically in the form of a patch located some distance from the target tissue) will also be employed as is standard practice in electrosurgical methods.

A supplemental electrode carrying a supplemental electrical current is used in addition to the primary electrodes, and the supplemental electrical current creates a supplemental magnetic field according to the laws of electromagnetism. The supplemental electrode is preferably insulated from the treatment tissue (e.g., insulated by air or by an insulated sheath surrounding the supplemental electrode). Because of the proximity of the supplemental electrode to the primary electrodes, the supplementary magnetic field interacts with the electromagnetic field created by the primary electrodes. This interaction allows characteristics of the primary electric current (e.g., current path, current density, etc.) to be manipulated at the discretion of the user.

For previously-available two-electrode RF electrosurgical devices, the electrical current density profile in the treatment tissue varies inversely with the depth below the surface of the treatment tissue. Thus, regions of higher current density are found in the surface layers of the treatment tissue relative to the current density that is present with increasing depth below the surface of the tissue.

Figure 7:
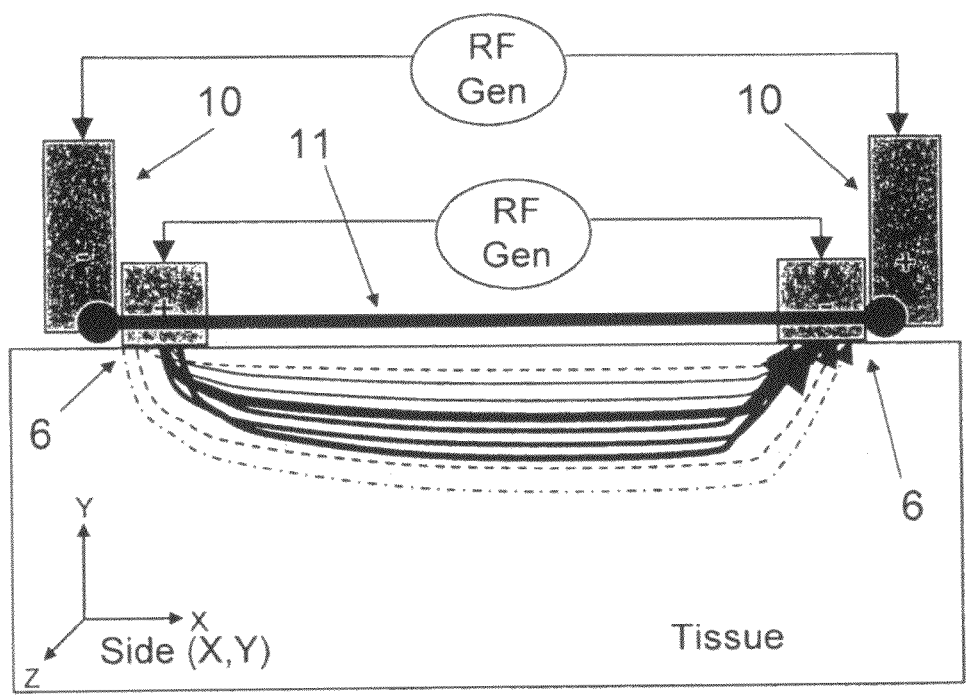
FIG. 7 shows a schematic representation of electrical current flow through a target tissue in the presence of a supplemental magnetic field. The current is created by a potential that exists between primary electrodes, and the supplemental magnetic field is created by a supplemental current flowing through the supplemental wire as disclosed herein.

The current density profile created by operation of the electrosurgical devices of the disclosure differs from those of traditional devices. Without wishing to be bound by theory, the path and density of the primary electrical current is influenced by the interaction between the electromagnetic field and the supplemental magnetic field. For example, use of a supplemental magnetic field that opposes the primary magnetic field results in a reduction in the intensity of the overall (i.e., summation) magnetic field near the surface of the treatment site. Altering the overall magnetic field in the vicinity of the target site does not, however, alter the total amount of current flowing between the primary electrodes (i.e., the magnitude of the primary current). The magnitude of the primary current is a function of the power supplied by the primary power supply, not the magnetic field in the treatment tissue. By reducing the total magnetic field near the surface of the treatment site, yet keeping the total power flowing through the target tissue constant, the regions of higher current density for the primary electrical current move deeper into the target tissue. This concept is shown in FIG. 7, and is referred to herein as a "modified current density gradient." It will be appreciated that the modified current density gradient created by the electrosurgical devices of the disclosure do not necessarily involve all of the uppermost layers of the treatment tissue. That is, the electrical current within the treatment tissue may not necessarily be a direct function of depth below the surface of the tissue at all depths. In some cases, one or more layers of tissue at or near the surface may carry more current than the layer of tissue directly below the layer.

In a preferred embodiment, the primary electromagnetic field creates a current at a first depth below the surface of the target tissue, and a current at a second depth below the surface of the target tissue. As the terms are used herein, tissue at a "first depth" is closer to the surface of the tissue than tissue at a "second depth." In the absence of the supplemental magnetic field, the primary electromagnetic field creates a current density gradient that varies inversely with depth below the surface of the tissue (i.e., current at a first depth is greater than current at a second depth). The current density gradient created by the primary electromagnetic field in the presence of the supplemental magnetic field may also be inversely proportional to the depth below the surface, or may be inversely proportional (i.e., current at a first depth is less than current at a second depth). When inversely proportionate, however, the supplemental magnetic field will modify the current density gradient such that the current at the first depth is less when the supplemental magnetic field is present than when the supplemental magnetic field is absent. In addition, and as described herein, the total current through the tissue remains constant whether the supplemental magnetic field is present or absent. Thus, when the current at the first depth decreases due to the presence of the supplemental magnetic field, there is correspondingly an increase in the current at the second depth. Due to this interaction between the primary electromagnetic field and the supplemental magnetic field, for example, a greater amount of energy can be applied to the tissue without observing undesired tissue effects. In preferred embodiments, for example, the current at the second depth is increased to a level sufficient to cause the desired tissue effect (e.g., contraction of collagen), while the current at the first depth remains below the level sufficient to cause undesired effects (e.g., pain, charring, or ablation).

Applying electrical currents to biological tissue may cause an increase in the temperature of the tissue. Accordingly, the modified current density gradient described above creates a modified thermal gradient in the treatment tissue—i.e., using the electrosurgical devices of the disclosure to treat a target tissue, the temperature of the tissue located below the surface layers of the tissue increases more than the temperature of the surface layers of tissue. The supplemental magnetic field can be used to influence the temperature gradient within the treatment tissue as a function of depth below the surface of the tissue. Thus, the devices of the disclosure are useful in non-homogeneously increasing the temperature of the target tissue.

In another embodiment of the disclosure, there is provided an electrosurgical device comprising a means for creating a magnetic field and further comprising a passive element. The devices according to this embodiment are suitable for a method for inducing an electrical current in a tissue comprising applying an magnetic field to the tissue and contacting a surface of the tissue with the passive element.

The means for creating a magnetic field (also referred to herein as a magnetic field generator or primary magnetic field generator) may be any device, element, or combination of devices that generates a magnetic field. In a preferred embodiment, the magnetic field generator comprises one or more conductors electrically coupled to a power source. Suitable power sources provide an AC signal. In a preferred embodiment, the frequency of the AC signal is about 1 MHz, although the disclosure encompasses instances wherein the frequency is less than 1 MHz (e.g., less than 800 kHz, or less than 500 kHz, or as little as 100 kHz), as well as instances wherein the frequency is greater than 1 MHz (e.g., 1.2 MHz, or 1.5 MHz, or more).

The one or more conductors are any conductors suitable for providing a magnetic field (also referred to herein as a primary magnetic field) that interacts with the treatment tissue. The magnetic field generator In preferred embodiments, the one or more conductors comprises an inductor. Suitable inductors, as described herein supra, include coils, spirals, combinations thereof, and similar components having a ferromagnetic material as a core material. A preferred inductor is an electromagnet (i.e., a metallic wire coiled around a ferromagnetic material).

The one or more conductors are disposed on a treatment probe, or housed within a treatment probe. In preferred embodiments, the treatment probe containing the one or more conductors also contains the passive element. For example, the passive element may be disposed on a treatment surface of the treatment probe.

The passive element is adapted to contact the tissue and provide a path of low electrical resistance between two locations on the tissue. In preferred embodiments, the passive element has a resistivity that is less than the resistivity of the tissue. For example, in one embodiment the tissue is human skin, and the passive element has a resistivity that is less than the resistivity of the tissue. As a further example, in some preferred embodiments, the passive element has a resistivity that is less than 1 ohm-m, or less than 0.1 ohm-m, or less than 0.01 ohm-m, or less than 0.001 ohm-m, or equivalent to that of a metal such as gold, silver, aluminum, copper, iron, or stainless steel.

The passive element is not connected to a power source, or, alternatively, is connected to a power source that is in the off- or standby-position.

In some embodiments, the passive element is configured to simultaneously contact the biological tissue in at least two isolated locations separated by a region of tissue, and the passive element does not contact the tissue in the region of tissue. In other embodiments, the passive element is configured to contact the biological tissue at a plurality of points along a continuous region of tissue. It will be appreciated that the devices described herein may comprise a plurality of passive elements each adapted to contact the tissue and provide a path of low electrical resistance between two locations on the tissue.

The passive elements may be, for example, electrodes having the size, shape, and distribution characteristics described herein for primary electrodes. More than one passive element may be used, and in a preferred embodiment, two passive elements are used. Furthermore, more than two passive elements may be used, and the region of tissue that is treated by the induced electrical current will generally be substantially within the area between the two outermost passive elements (i.e., the two passive elements that are furthest from each other, when applicable). Each passive elements may be any size or shape. During operation of the electrosurgical device, all or a portion of the passive elements are brought into electrical and physical contact with the treatment tissue.

In one aspect of the invention, one or more passive elements are placed in contact with the treatment tissue. Where a plurality of passive elements are used, any two or more passive elements may be connected to each other by a conductive connecting element, such that the connected passive elements are at the same electrical potential. The magnetic field generator (e.g., the one or more conductors coupled to a power source) is placed in close proximity to the treatment tissue, and creates a magnetic field that induces electrical current within the treatment tissue. The magnetic field described previously interacts with the tissue and generates an induced electric current in the target tissue. The induced electric current flows along a closed loop that includes the treatment tissue, the passive elements, and the conductive connecting element.

In another aspect of the invention, the conductive connecting element directly contacts the treatment tissue during operation of the electrosurgical device. In such an embodiment, the conductive connecting element also functions as the passive elements. FIG. 8 provides an example of an electrosurgical device employing passive elements and a conductive connecting element.

Generally, the induced electrical current will have a current density profile that is suitable for treating the lower layers of tissue in the treatment tissue. A component of the induced current that is substantially parallel to the surface of the treatment tissue will therefore be concentrated in the lower layers of the treatment tissue. For example, when the treatment tissue is skin, a region of relatively high current density will be present during treatment below the stratum corneum, or below the epidermis, or below the hypodermis. In this manner, the induced current may be used to heat the lower layers of tissue in the treatment tissue. The path of the current in the lower layers of the treatment tissue can be adjusted by suitably modifying parameters of the magnetic field (e.g., magnitude, orientation, etc.).

To create a closed circuit loop for the induced electrical current, the passive elements are electrically connected by a conducting connecting element, or the conducting connecting element contacts the target tissue. Generally, the conducting connecting element and the passive elements have a lower resistivity compared with the target tissue. The conducting element may be any appropriate size or shape. For example, a metal plate or wire may be used as the conductive element. Without wishing to be bound by theory, it is believed that the conducting connecting element and passive element prevents a substantial amount (>10%, or >25%, or >50%, or >75%, or >90%, or >95%, or >99%) of the current generated by the primary magnetic field from flowing through the uppermost layers of the treatment tissue by offering a path of lower electrical resistance. Diverting a substantial amount of the current through the conductive connecting element and passive elements allow minimal increases in temperature of the uppermost layers of tissue.

The passive elements, conducting connecting element, and inductor portion of the primary magnetic field generator may be disposed on a single electrosurgical probe. Alternatively, any of these elements or portions of any of these elements may be located on a separate probe. The inductor portion of the magnetic field generator is electrically connected to a power supply, as described previously herein.

As described supra for devices employing primary electrodes, devices employing a conductive connecting element and passive elements may be used to create a modified thermal gradient in the target tissue. In all of the devices described herein, the temperature gradient within the target tissue may be varied by varying the intensity of the applied primary or supplemental magnetic field. For example, the region of tissue that is heated may be forced deeper into the tissue by appropriately varying the applied magnetic field.

In one embodiment, the target site is skin, and the electrosurgical device is placed in close proximity to the surface of the skin so as to generate an electric field that causes a current to flow through the stratum corneum, epidermis, dermis, and hypodermis. By creating an electrical current within the skin, the devices disclosed herein are able to increase the temperature of the skin, and in some cases, treat differentially one or more layers of skin. For example, when operating the devices of the disclosure without applying the supplemental magnetic field, the devices are useful in fully or partially ablating the surface of the skin. When operating the devices of the disclosure along with the supplemental magnetic field, the devices are useful in partially or fully treating (ablative or non-ablative) one or more layers below the surface of the skin. The treatment depth (i.e., the depth of the layers of skin that are treated) may be adjusted by changing characteristics of the supplemental magnetic field such as magnitude and direction. Furthermore, the temperature or increase in temperature of the target tissue can be controlled at any desired depth in the target tissue by controlling the supplemental magnetic field.

The electrosurgical probe may be translated (i.e., moved) parallel to the skin surface during the application of electrical energy to the skin. Such translation may occur with the probe either in contact with the skin or in close proximity to the skin. Translation of the probe allows for enlarged areas of treatment, improved heat dissipation, and other benefits as will be appreciated by the skilled artisan. The power source(s) can also be programmed and controlled, using standard control circuitry, to apply RF energy to the electrodes in a time-dependent fashion, such that specific treatment patterns are created based on the rate and direction of translation of the electrosurgical probe.

Electrical energy may be delivered to the electrosurgical probes either continuously or discontinuously. For continuous delivery of energy, the energy may be constant or may be varied in any suitable manner (such as cyclically, randomly, or according to a preset pattern). For discontinuous delivery of energy, the energy may be supplied and discontinued in any suitable manner (such as randomly or according to a preset pattern). The electrosurgical devices disclosed herein may, for example, be operated in pulsed or continuous mode.

Electrical energy applied via the electrosurgical devices disclosed herein may be used to heat, but not destroy and/or damage, the target site. For example, when the target site is skin, heat may be applied to treat the appearance of aging, acne, cellulite, or wrinkles (e.g., via collagen remodeling).

In one embodiment, the electrosurgical device is adapted for treating the skin. The device generates an electric field which causes a current to flow through the stratum corneum, epidermis, and/or dermis, and comprises a means for reducing or increasing the power dissipated in the stratum corneum relative to the deeper layers of tissue in the epidermis and/or dermis and/or hypodermis. Furthermore, heat delivered to the tissue may be useful in therapy of specific dermatological and non-dermatological disorders, and the methods and devices of the disclosure provide targeted heating of tissue for enhanced treatment of such conditions. Optimal therapy is achieved once energy is delivered differentially to specific targets of therapy. Non-limiting examples of targeted delivery of energy for treating various conditions include: more heat generated in the dermis and less heat in the epidermis for therapy of wrinkles; more heat generated at a hair follicle and less in the epidermis and dermis for hair removal; more heat generated at sebaceous glands and less in the epidermis and dermis for efficient acne therapy; and more at dermal and hypodermal structures and less heat provided at the epidermis for Cellulite therapy.

In other embodiments, the electrosurgical devices of the disclosure are adapted for treating organs, mucous membranes, blood vessels, hair and/or hair follicles (e.g., hair removal), or another body structures.

Electrical and/or physical characteristics of the primary electrodes (e.g., current, potential, temperature, etc.) may be measured and monitored by appropriate circuitry. Alternatively or in addition, electrical and/or physical characteristics of the treatment tissue may be monitored by sensors. Such sensors may be located on the electrosurgical probes of the disclosure, or may be provided separately. Measurements may be taken in real time as the electrosurgical probes of the invention are in use. The devices of the disclosure may include circuitry that adjusts the power provided to the primary electrodes and/or to the supplementary wire in response to the such measured characteristics.

The devices disclosed herein may be used in conjunction with the phase-controlled RF technology described in co-pending U.S. patent application Ser. No. 11/654,914, filed Jan. 17, 2007, the contents of which is herein incorporated by reference in its entirety.

The RF devices and methods as disclosed herein may be combined with other sources of energy. In some embodiments, the use of additional forms of energy allow synergistic effects for treatment of conditions such as skin disorders, skin aging and hair removal. For example, focused ultrasound energy may cause micro-vibrations in susceptible living tissue. The micro-vibrations caused by the ultrasound differ for different types of tissue (e.g., skin; keratinocytes or epidermal cells, hard keratin such as the shaft of hairs, etc.). Focused ultrasound energy can differentiate physical properties of living tissue (e.g., treated from untreated tissue during electrosurgical procedures, adipose subdermal cells from connective tissue cells, etc.). In one embodiment of the methods and devices disclosed herein, RF and ultrasound energy are used to treat tissue. Examples of uses for the combination of RF and ultrasound energy include the removal of hair and therapy of cellulite (e.g., hair removal or therapy that is safer and more efficient than existing methods).

The electrosurgical methods and devices disclosed herein may also be used in conjunction with an additional means for applying energy such as light energy to the target site. For example, the electrosurgical probe may comprise an optical light source (e.g., lasers, incandescent lamps, gas-discharge lamps, LEDs, and the like), an infrared light source, an ultraviolet light source, or any combination thereof. Such additional means for applying energy may be electrically coupled to the same power source(s) that provide power to the electrodes of the electrosurgical probe, or may be electrically coupled to a separate power source.

In another embodiment, the electrosurgical device may include a means for lowering the temperature of the surface of the target site. Such means include electrical cooling devices such as a heat sink and delivery ports for delivering cooling liquids or gases to the target site and surrounding tissue. For example, electrical contact cooling allows cooling of portions of the target site such as the epidermis, thereby minimizing pain and heat damage to surrounding (i.e., perilesional) skin.

In another embodiment, the treatment portion (e.g., head or tip) of the electrosurgical probe of the device comprises a mechanism that allows all or a portion of the electrosurgical probe to mechanically vibrate during use. Such vibrations allow the treatment site to be massaged or otherwise soothed. This feature is especially preferred when the device is used to treat cellulite as described herein.

The methods disclosed herein may further comprise a pre-treatment step such as: treatment with a topical anesthetic; cooling; and treatment with light energy. Topical anesthetics such as lidocaine and the like may be applied as needed, such as 30-60 minutes prior to treatment with the electrosurgical device. Cooling of the target site as a pretreatment step may involve application of cooling agents such as gels, liquids, or gases. Examples include water and saline solutions, liquid nitrogen, carbon dioxide, air, and the like. Cooling may also involve electrical contact cooling. Typically, cooling of the target site is accomplished just prior to treatment with the electrosurgical probe, and has the effect of reducing pain and unwanted heat damage to the tissue surrounding the target site. Pretreatment with light energy may be accomplished using a light source integrated with the electrosurgical probe or with a separate light source. Light energy is capable of effecting photothermolysis, and is useful in selectively heating regions of the target area. Accordingly, light energy can be used in conjunction with the electrosurgical devices. For example, regions of darker coloration such as hair and skin characterized by the presence of relatively large amounts of melanin (e.g., moles, hyperpigmented lesions, and the like) may be selectively heated, as such areas will absorb more light energy compared with regions with less pigmentation. Light energy may also be used to create preferred conduction pathways for the electrical currents that are produced by the electrosurgical probes described herein. Methods of treatment using light energy as well as the electrosurgical devices disclosed herein are particularly suitable for the treatment of hyperpigmented lesions, melasma, lentigines, wrinkles, and acne scars, as well as in hair removal, and the clearing of vascular lesions.

After treatment of the target site with the electrosurgical devices described herein, certain post-treatment steps may also be taken. Such post-treatment steps include treatment with a topical anesthetic as described above, and cooling of the target site and surrounding tissue as described above.

The devices of the disclosure will now be described by reference to the embodiments illustrated by the various figures provided herein. It will be appreciated, however, that such figures are provided only for the sake of illustration, and are not meant to be limiting in any way.

Figure 1B:
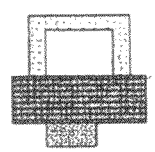

FIG. 1a shows an electrosurgical device comprising an electrosurgical probe 1 electrically coupled to a power source 2. Electrosurgical probe 1 comprises handle 3 and treatment surface 4. Power source 2 may also function as a control unit. The electrosurgical device can be adapted for "cordless" operation, and FIG. 1b shows an electrosurgical device that combines an electrosurgical probe with a battery pack (not shown).

Figure 2A:
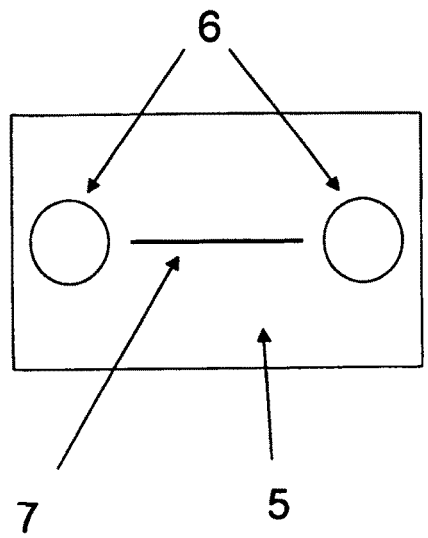
FIGS. 2a, and 2b are example illustrations of treatment surfaces of electrosurgical probes as disclosed herein.
Figure 2B:
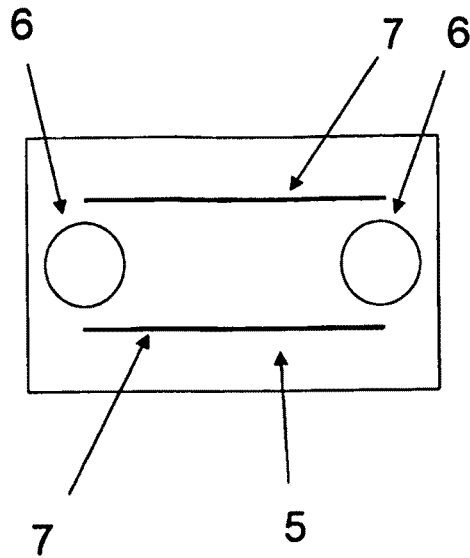
Figure 2C:
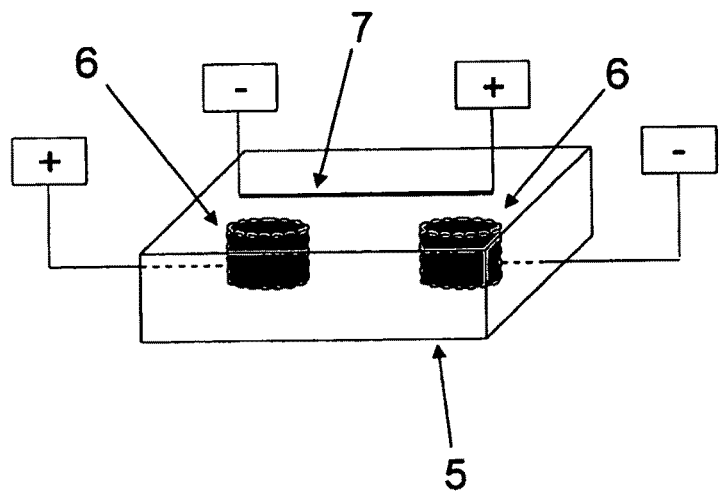
FIG. 2c is an example illustration of a treatment portion of an electrosurgical probe as described herein.

FIGS. 2a and 2b show examples of different treatment surfaces of electrosurgical probes according to the disclosure. Treatment surface 5 comprises a plurality of electrodes 6 and one or more supplemental wire(s) 7. FIG. 2c shows yet another arrangement for the treatment portion of an electrosurgical probe, wherein supplemental wire 7 is disposed on top of the treatment portion. Alternatively, the supplemental wire may be embedded within the treatment portion of the electrosurgical probe. It will be appreciated that the treatment portion of the electrosurgical probe will not completely magnetically shield the supplemental wire from the treatment site in embodiments according to the disclosure.

Figure 3A:
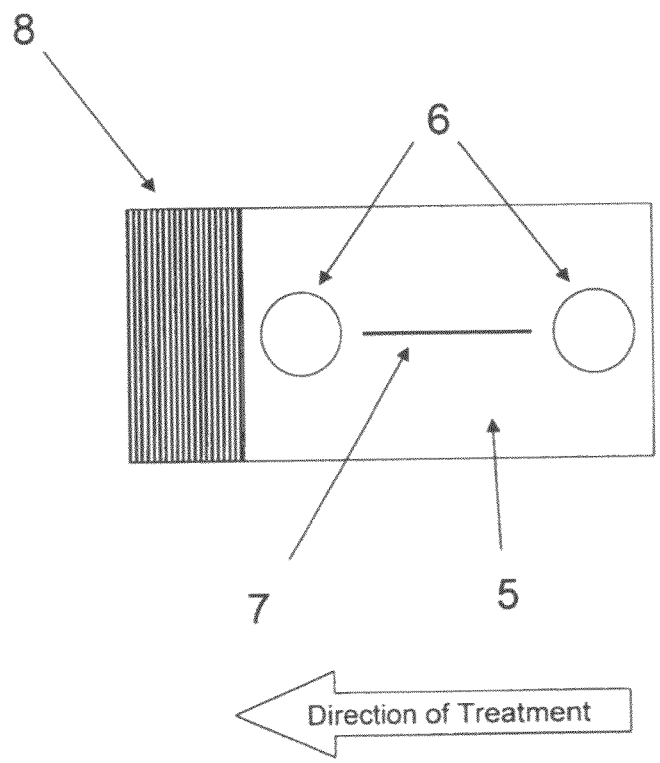
FIGS. 3a, 3b, and 3c are example illustrations of treatment surfaces of electrosurgical probes as disclosed herein.
Figure 3B:
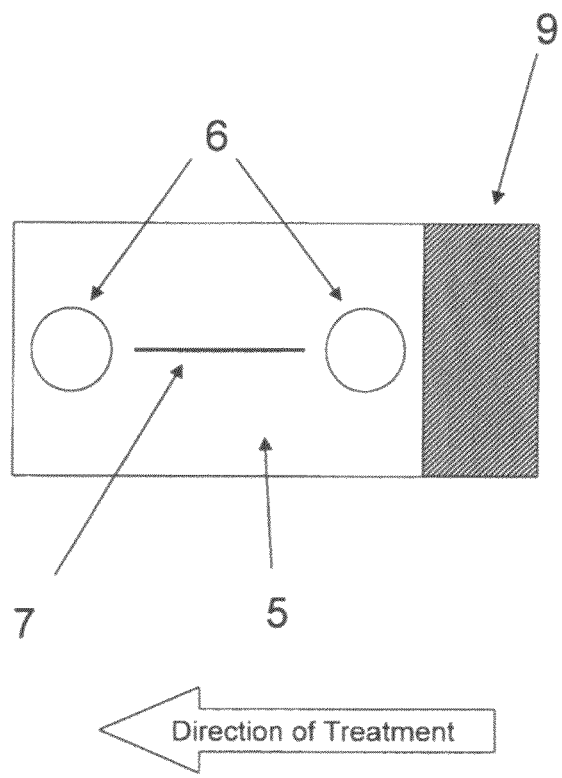
Figure 3C:
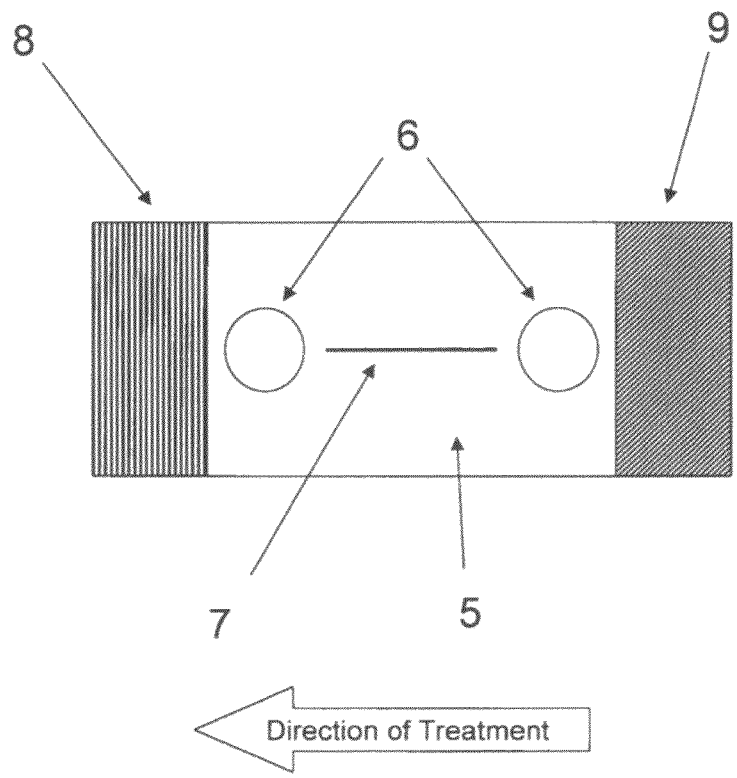

Various embodiments of the electrosurgical probes disclosed herein are shown in FIGS. 3a-3c. FIG. 3a shows the treatment surface of an electrosurgical probe containing pretreatment device 8. FIG. 3b shows the treatment surface of an electrosurgical probe containing post-treatment device 9. FIG. 3c shows the treatment surface of an electrosurgical probe containing pre-treatment device 8 and post-treatment device 9.

Figure 4:
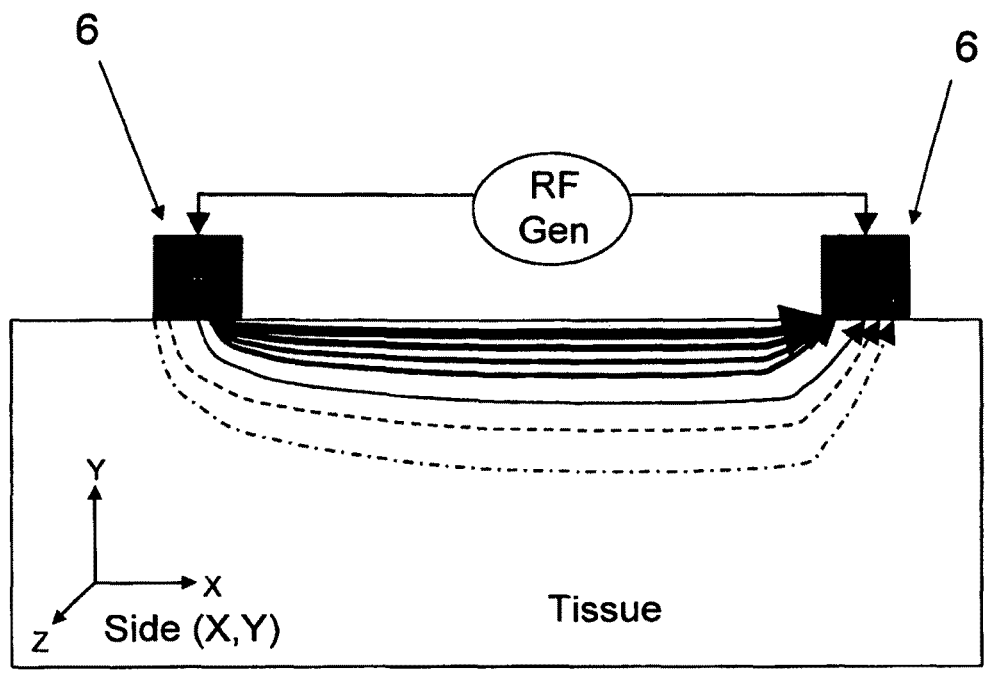
FIG. 4 shows a schematic representation of electrical current flow through a target tissue in the absence of a supplemental magnetic field. The current is created by a potential that exists between primary electrodes as disclosed herein.

FIG. 4 shows a schematic representation of electrical current flow through a target tissue in the absence of a supplemental magnetic field. Primary electrodes 6, which are disposed on the treatment surface of an electrosurgical probe (not shown), are in contact with the target tissue and are furthermore electrically coupled to a power source (also not shown). The current is created by a potential that exists between primary electrodes as disclosed herein. A normal current gradient exists, meaning that the electrical current density varies inversely with depth below the surface of the target tissue. In FIG. 4 (as well as in other figures), the electrical current path is represented by arrows (e.g., extending between the electrodes 6). Line thickness and dashing is used to indicate the magnitude of electrical current.

Figure 5A:
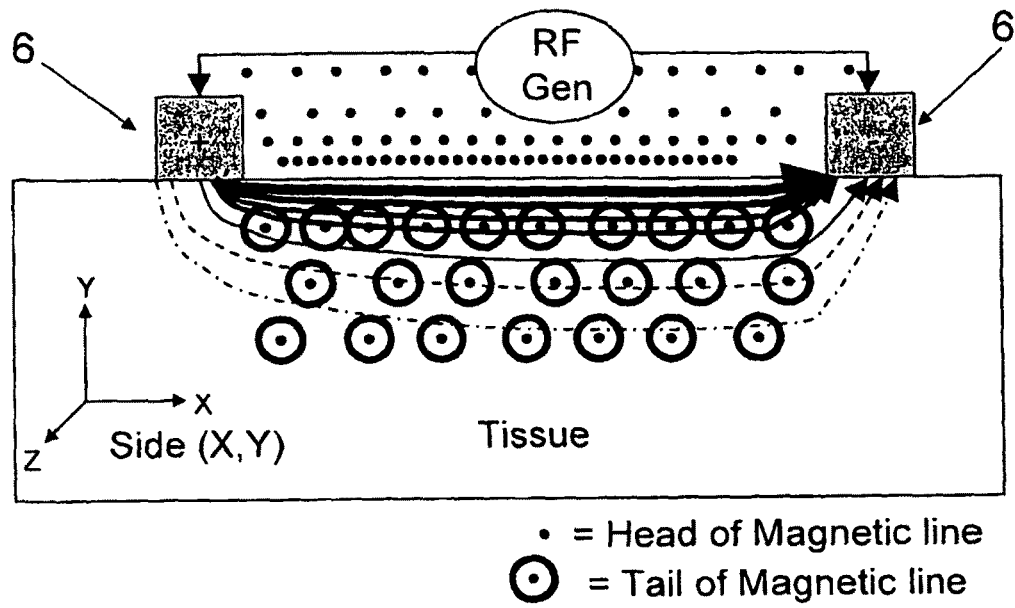
FIGS. 5a and 5b are different views of a schematic representation of the magnetic field created by the electrical current flow illustrated in FIG. 4.
Figure 5B:
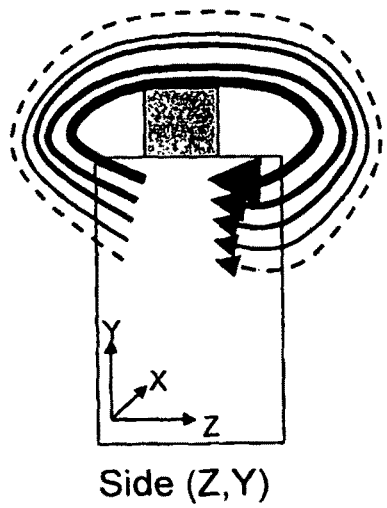

FIGS. 5a and 5b are different views of a schematic representation of the magnetic field created by the electrical current flow illustrated in FIG. 4. As shown by the thickness of the magnetic field lines in FIG. 5b, the magnetic field is greatest near the surface of the target tissue.

Figure 6A:
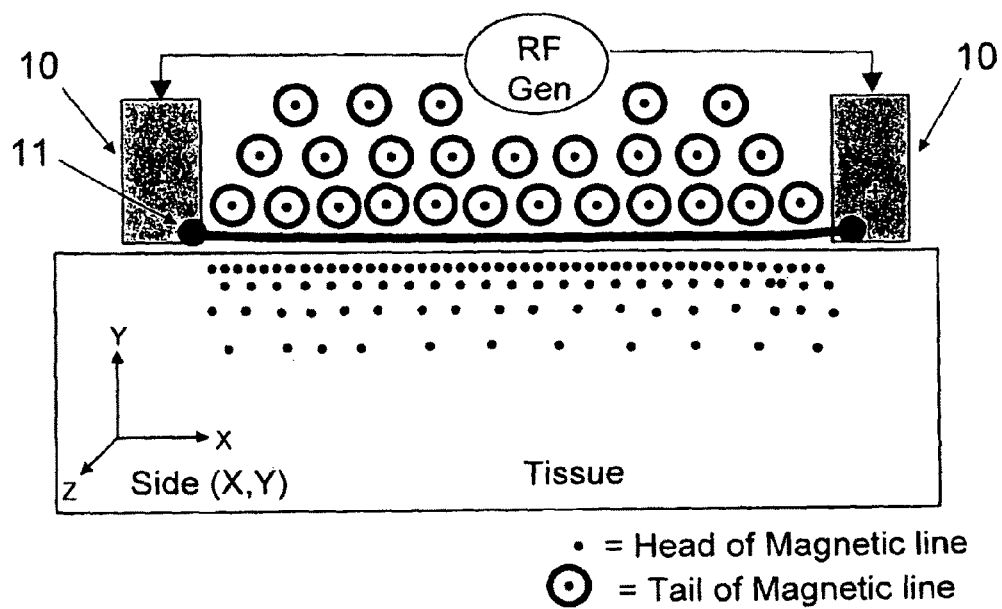
FIGS. 6a and 6b are different views of a schematic representation of the magnetic field created by an electrical current flowing through a supplemental wire as disclosed herein.
Figure 6B:
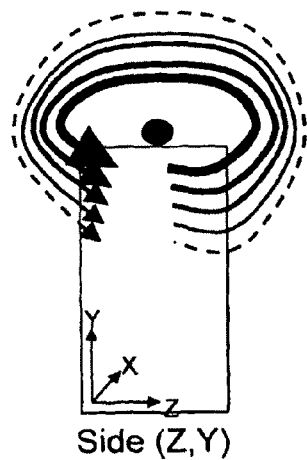

FIGS. 6a and 6b are different views of a schematic representation of the magnetic field created by an electrical current flowing through supplemental wire as disclosed herein. Units 10 represent the electrical connection of supplemental wire 11 and the RF generator shown in the Figure. Supplemental wire 11 does not contact the treatment tissue. As shown by the thickness of the magnetic field lines in FIG. 6b, the magnetic field is greatest near the surface of the target tissue, but has a polarity that is reversed relative to the polarity of the magnetic field shown in FIG. 5b. Although the Figure shows supplemental wire 11 connecting to the RF generator through units 10 (which may be provided, for example, for structural support or to aid electrical connections for supplemental wire 11) it is important to note that units 10 are optional, and supplemental wire 11 may be directly connected to the RF generator.

FIG. 7 shows a schematic representation of electrical current flow through a target tissue in the presence of a supplemental magnetic field. The electrical current in the target tissue is created as for FIG. 4. The supplemental magnetic field is created as for FIGS. 6a and 6b. In the Figure, the supplemental magnetic field opposes the primary magnetic field, thereby forcing more of the current density of the primary current through the target tissue to shift lower within the tissue (relative to FIG. 4, i.e., in the absence of the supplemental magnetic field). Supplemental wire 11 connects to the RF generator through connection units 10, but does not make electrical contact with electrodes 6 or with the target tissue.

Figure 8A:
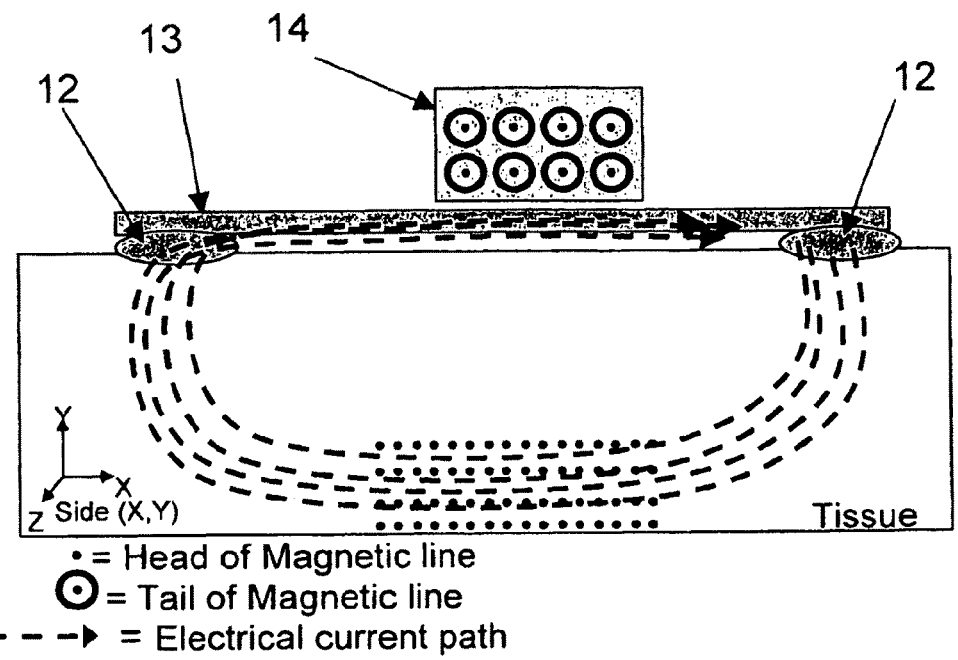
FIGS. 8a and 8b are different views of a schematic representation of the magnetic field and electrical current created by an electrosurgical device employing a primary magnetic field generator and passive electrodes as disclosed herein.
Figure 8B:
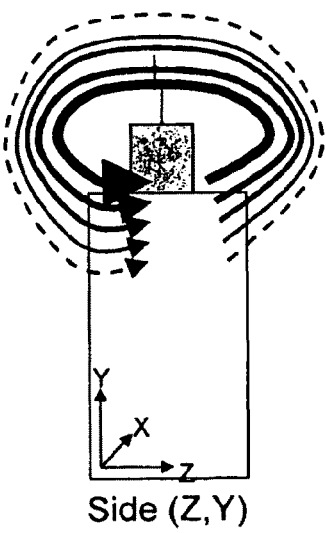

FIGS. 8a and 8b shows a schematic representation of electrical current flow in a treatment tissue generated by an inductive electrosurgical device. A power supply (not shown) supplies power to inductor 14 in order to generate a primary magnetic field (indicated by dots and circled dots) that gives rise to an electrical current in the target tissue (indicated by dashed arrows). Passive electrodes 12 contact both the treatment tissue and conductive element 13, providing a current path that is an alternative to the surface layers of the treatment tissue. The depth of the electrical current path in the target tissue is determined by the primary magnetic field, which is influenced by the operating parameters of the magnetic field generator.

The methods and devices disclosed herein are useful in the field of electrosurgery in general, and more specifically in procedures that are suitable for treatment using RF energy. A particular benefit of the methods and devices of the disclosure is that the temperature at a variety of depths below the surface of the target tissue can be controlled via the supplemental magnetic field. For example, by using a supplemental magnetic field that forces the majority of the primary current to flow below the surface layers of the target tissue, the surface layers of tissue can be kept cool while the underlying layers may be ablated or heated for treatment. Such methods may be useful, for example, in treating the skin of a patient while minimizing visual or physical effects (e.g., scarring, pain, etc.) of the treatment at the surface of the skin.

For example, the methods and devices disclosed herein may be employed in procedures useful in the treatment of medical and aesthetic disorders and conditions affecting a patient's skin and subcutaneous tissue, including the following: skin resurfacing procedures; lessening the appearance of or removal of pigmentations; lessening the appearance, removing, or otherwise treating cellulite; therapy or removal of wrinkles, vascular lesions, scars and tattoos; hair removal and hair transplant procedures; treatment of skin cancer; skin rejuvenation; treatment of acne and psoriasis; debridement of chronic skin ulcers; and blepharoplasty procedures.

The methods and devices disclosed herein are also useful in treating the signs of skin aging, including treatment of skin roughness, uneven pigmentation, wrinkles, and dilated capillaries. Cosmetic applications not related to skin aging (e.g., repair or removal of birthmarks, repair of damage caused by trauma or injuries, etc.) are also within the scope of the invention.

Many of the conditions and methods of treatment mentioned above make use of the devices of the disclosure and their ability to selectively heat tissue below the surface of the tissue being treated. For example, the devices disclosed herein are useful in methods for treating wrinkles and other signs of aging. Warming the collagen below the surface of the skin causes the collagen molecules to reorient on a molecular level, thereby eliminating or reducing the presence of wrinkles. The use of RF with a supplemental magnetic field allows selective heating of regions of collagen without causing heating or damage of surrounding areas.

Typically, although not necessarily, users of the devices and methods disclosed herein are doctors or other medical health professionals working, for example, in a hospital or clinic. Devices and methods that are suitable for mobile use and/or for use by the patient (i.e., for self-treatment) are also within the scope of the disclosure. Mobile and self-treatment devices may be the same as, or different from devices intended for use in hospitals or clinics, and such differences will be apparent to the skilled artisan. For example, the mobile or self-treatment devices may be limited to operation at lower power, or the primary and/or supplementary power supplies may be incorporated into the devices.

The electrosurgical probe may be disposable, such that it is sterilized upon manufacture and is intended for a one-time use. Alternatively, the electrosurgical probe may be sterilizable (e.g., autoclavable) such that it is suitable for multiple uses and, in particular, use with multiple patients.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

It is to be understood that while the invention has been described in conjunction with the preferred specific embodiments thereof, that the foregoing description as well as the examples that follow, are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains.

EXAMPLES

General procedures: Simulations were performed using HFSS V10.0 software (Ansoft Ltd., Pittsburgh, Pa.). "Sea water" was used to model tissue, while "aluminum" was used to model electrodes. Analyses were performed at 1 MHz. Simulations using primary (i.e., active) electrodes employed six electrodes, each having dimensions of 3 mm (width)×25 mm (length)×40 mm (height). Each electrode was stimulated with an ideal voltage source of 1 MHz sine signal of 100 V amplitude. Three electrodes were configured with phase 0° and three electrodes were configured with phase 180° forming a Phase Controlled effect. A global ground was used as reference for all Voltage sources. This global ground was positioned 50 mm over the tissue. Air was chosen as dielectric between the global ground and the tissue, as well as between the 6 electrodes. Finally, a coil was modeled using the same material as the electrodes, (i.e., "aluminium") and a core of air. An ideal current source was attached to the coil to generate a current flow. This current source was defined as 1 MHz, sine type and 15 Amperes. In each simulation, all six of the electrodes received power unless otherwise specified.

Images provided in the Figures describe the volumetric current density on an internal plane of the tissue (selected in the middle of the electrodes).

Example 1

Figure 9:
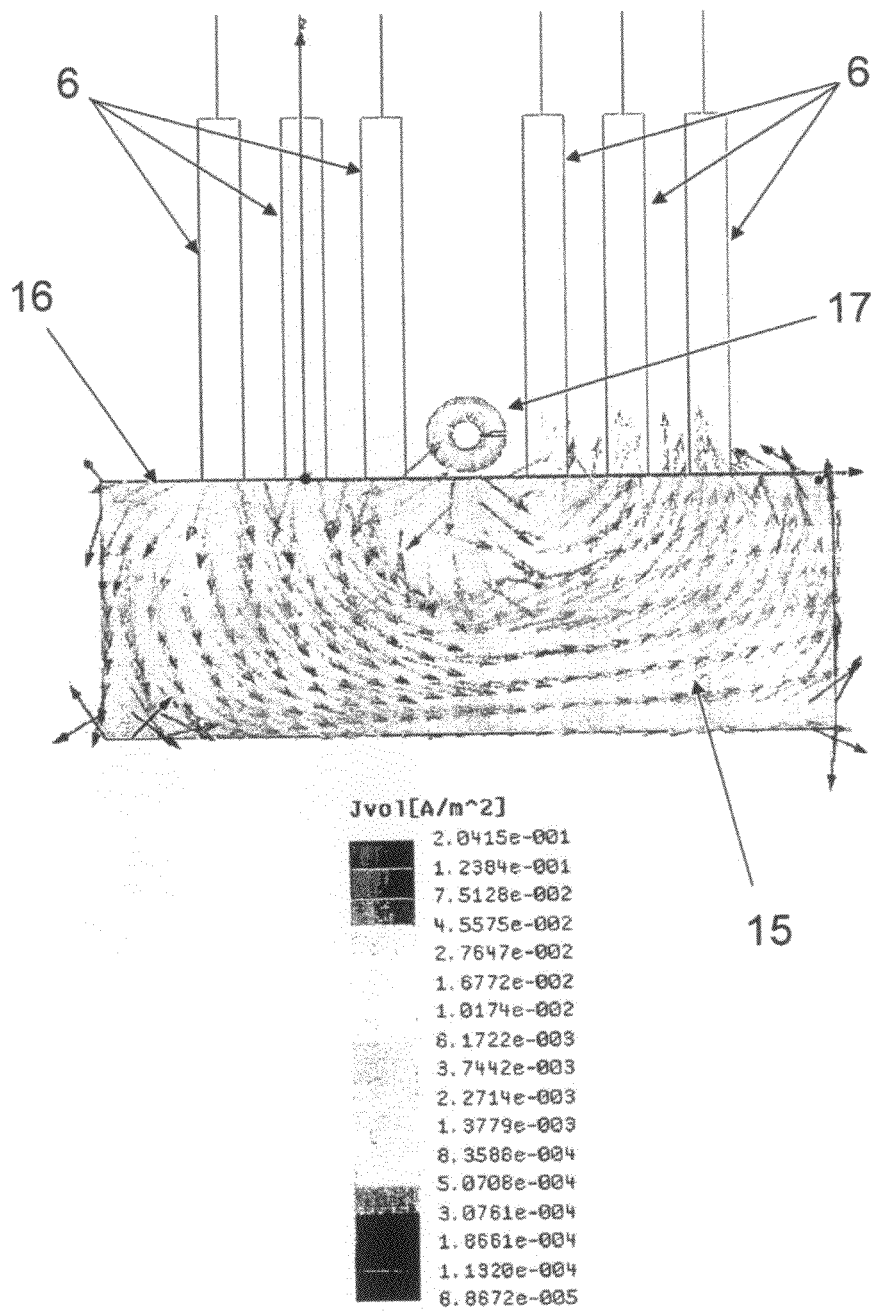
FIG. 9 shows volumetric current densities into the tissue with a supplemental magnetic effect.

Two computer simulations were performed to provide an illustration of some of the effects of an external (i.e., supplemental) magnetic field produced by an electrosurgical device. Results from the first simulation are illustrated in the current vector map in FIG. 9. Target region 15 provided a model for a treatment tissue such as skin. Electrodes 6 contacted target surface 16 and created an electric and magnetic field in target region 15. Supplemental coil 17 (not directly contacting target surface 16) received an electric current and generated a supplemental magnetic field (not shown). The electrical current density field is shown within the target region 10 as a series of arrows.

Figure 10:
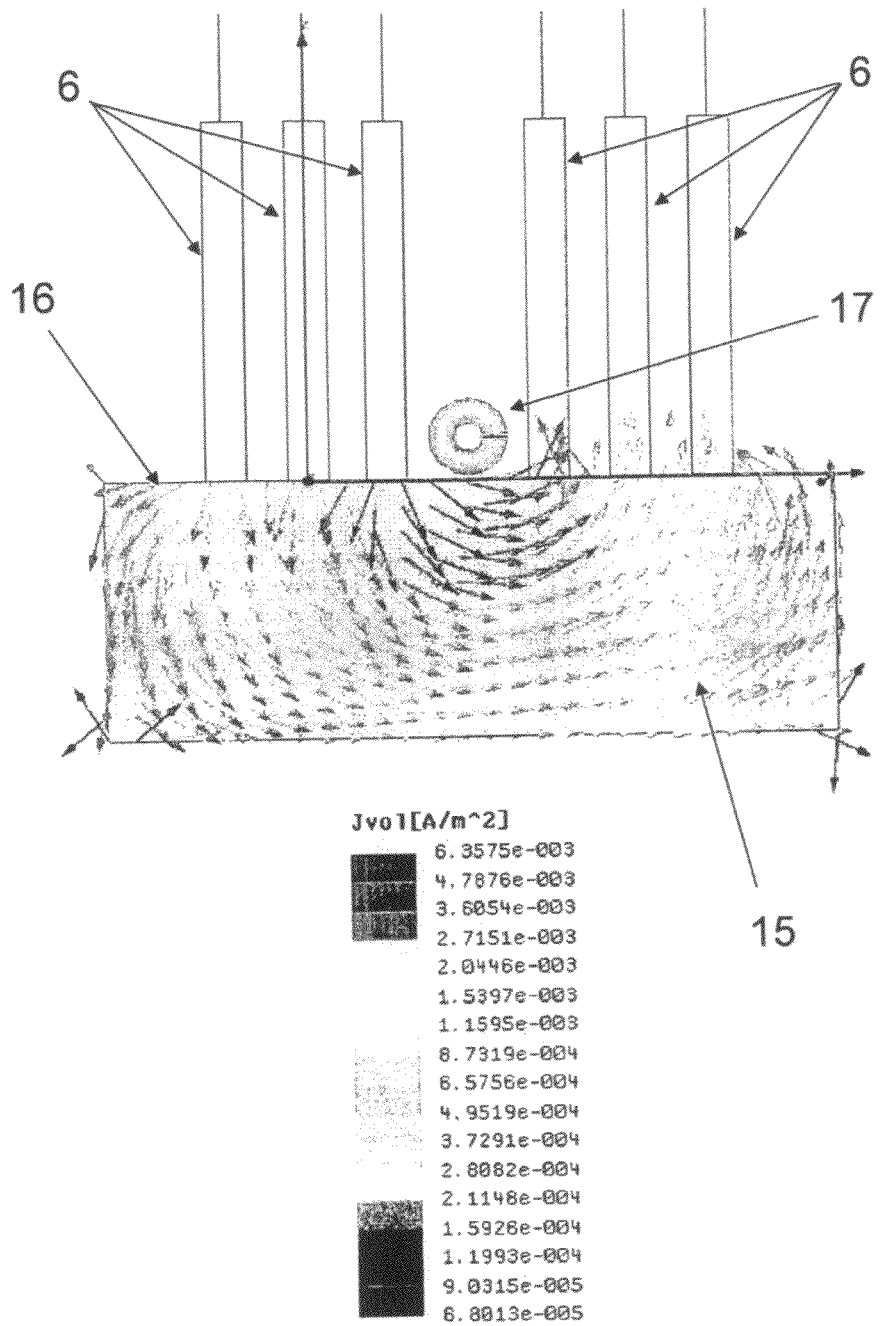
FIG. 10 shows volumetric current densities into the tissue without a supplemental magnetic effect.

Results from the second simulation are illustrated by the current vector map in FIG. 10. In the second simulation, no electrical current was provided to supplemental coil 17 (i.e., the coil was deactivated). Accordingly, no supplemental magnetic field was present in the target region 15.

It can be seen from the simulation data that the current density near target surface 16 is greater for the second simulation than for the first. This shows that the supplemental magnetic field supplied by supplemental coil 17 is effective in reducing the current density near the surface of the target tissue, thereby forcing more of the electrical current to flow through deeper layers in the target tissue.

Example 2

Figure 11:
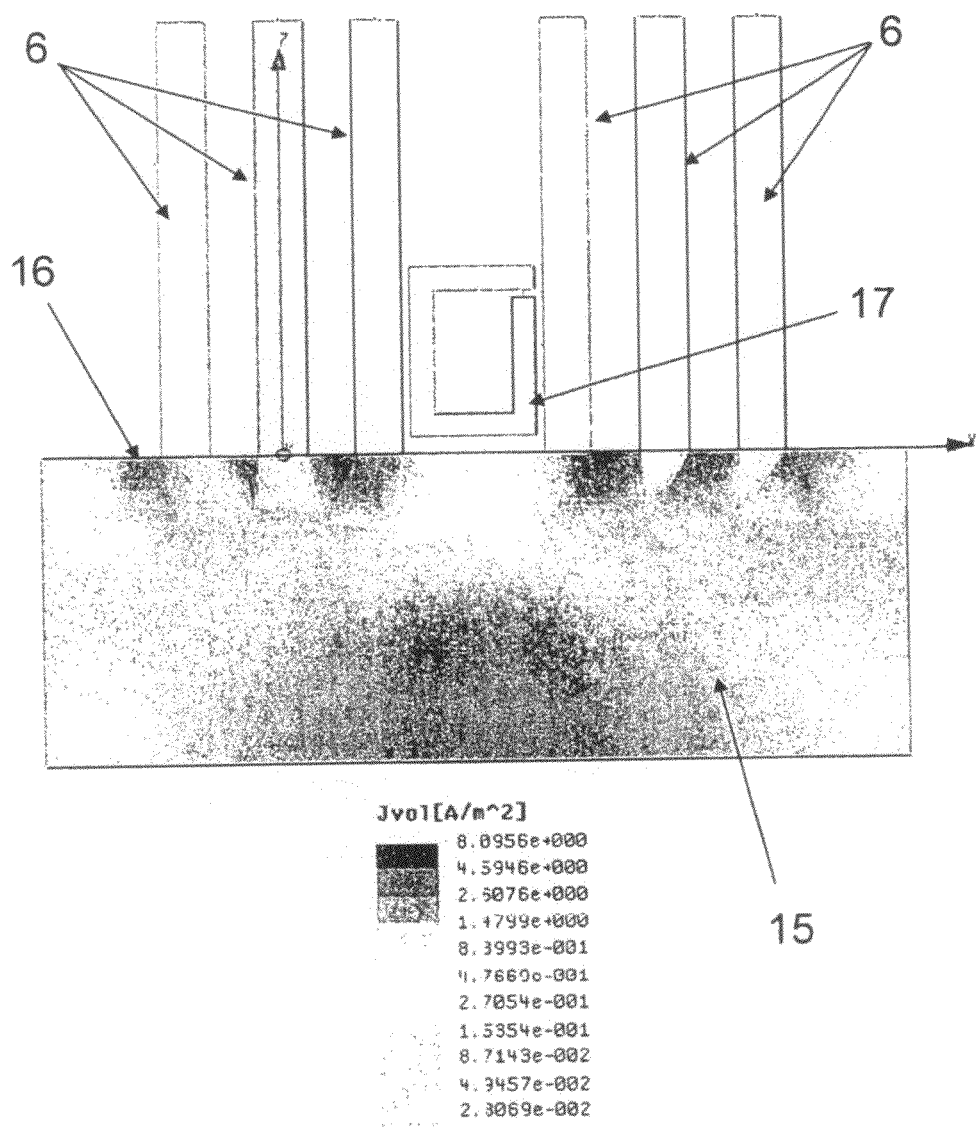
FIG. 11 shows current density in one internal plane of a tissue with a supplemental magnetic field.

Two computer simulations were performed to provide an illustration of some of the effects of an external (i.e., supplemental) magnetic field produced by an electrosurgical device. All six electrodes received power during the simulation. Results from the first simulation are shown in FIG. 11. Target region 15 provided a model for a treatment tissue such as skin. Electrodes 6 contacted target surface 16 and created an electric and magnetic field in target region 15. Supplemental coil 17 (not directly contacting target surface 16) received an electric current and generated a supplemental magnetic field (not shown). The electrical current density field is shown within the target region 15 as shaded regions.

Figure 12:
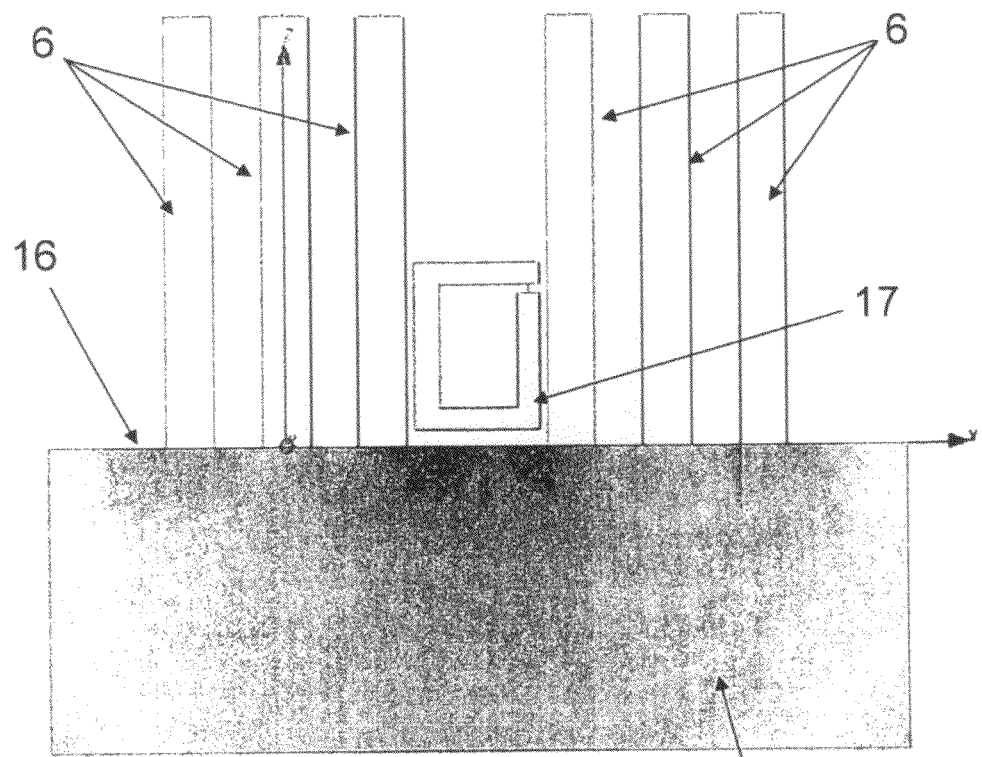
FIG. 12 shows current density in one internal plane of a tissue without a supplemental magnetic field.

Results from the second simulation are shown in FIG. 12. In the second simulation, no electrical current was provided to supplemental coil 17 (i.e., the coil was deactivated). Accordingly, no supplemental magnetic field was present in the target region 15.

It can be seen from the simulation data that the current density near target surface 16 is greater for the second simulation than for the first. This shows that the supplemental magnetic field supplied by supplemental coil 17 is effective in reducing the current density near the surface of the target tissue, thereby forcing more of the electrical current to flow through deeper layers in the target tissue.

Example 3

Figure 13:
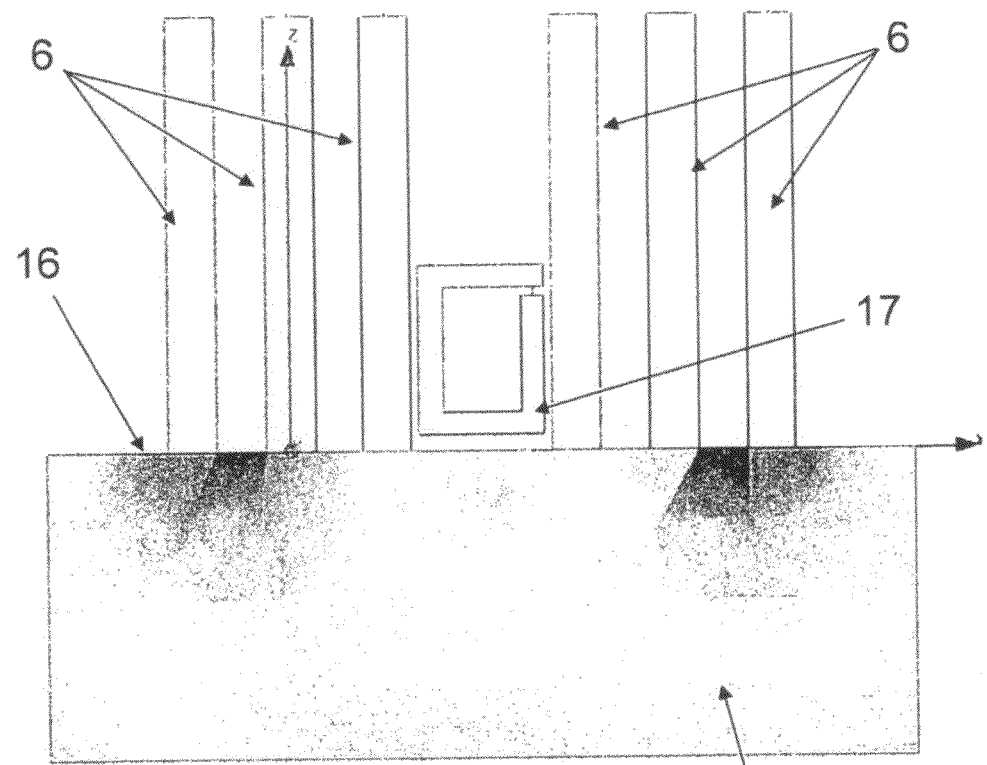
FIG. 13 shows current density in one internal plane of a tissue with a supplemental magnetic field.

Two computer simulations were performed to provide an illustration of some of the effects of an external (i.e., supplemental) magnetic field produced by an electrosurgical device. Two electrodes received power during the simulation. Results from the first simulation are shown in FIG. 13. Target region 15 provided a model for a treatment tissue such as skin. Electrodes 6 contacted target surface 16 and created an electric and magnetic field in target region 15. Supplemental coil 17 (not directly contacting target surface 16) received an electric current and generated a supplemental magnetic field (not shown). The electrical current density field is shown within the target region 15 as shaded regions.

Figure 14:
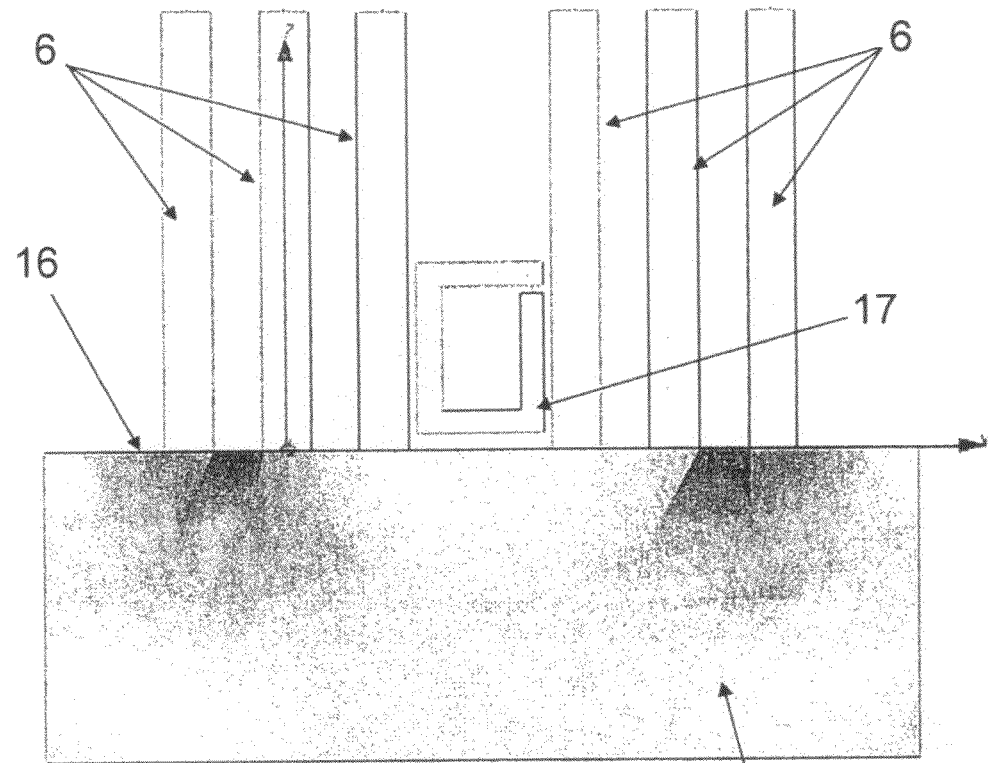
FIG. 14 shows current density in one internal plane of a tissue without a supplemental magnetic field.

Results from the second simulation are shown in FIG. 14. In the second simulation, no electrical current was provided to supplemental coil 17 (i.e., the coil was deactivated). Accordingly, no supplemental magnetic field was present in the target region 15.

It can be seen from the simulation data that the current density near target surface 16 is greater for the second simulation than for the first. This shows that the supplemental magnetic field supplied by supplemental coil 17 is effective in reducing the current density near the surface of the target tissue, thereby forcing more of the electrical current to flow through deeper layers in the target tissue.

Example 4

Figure 15:
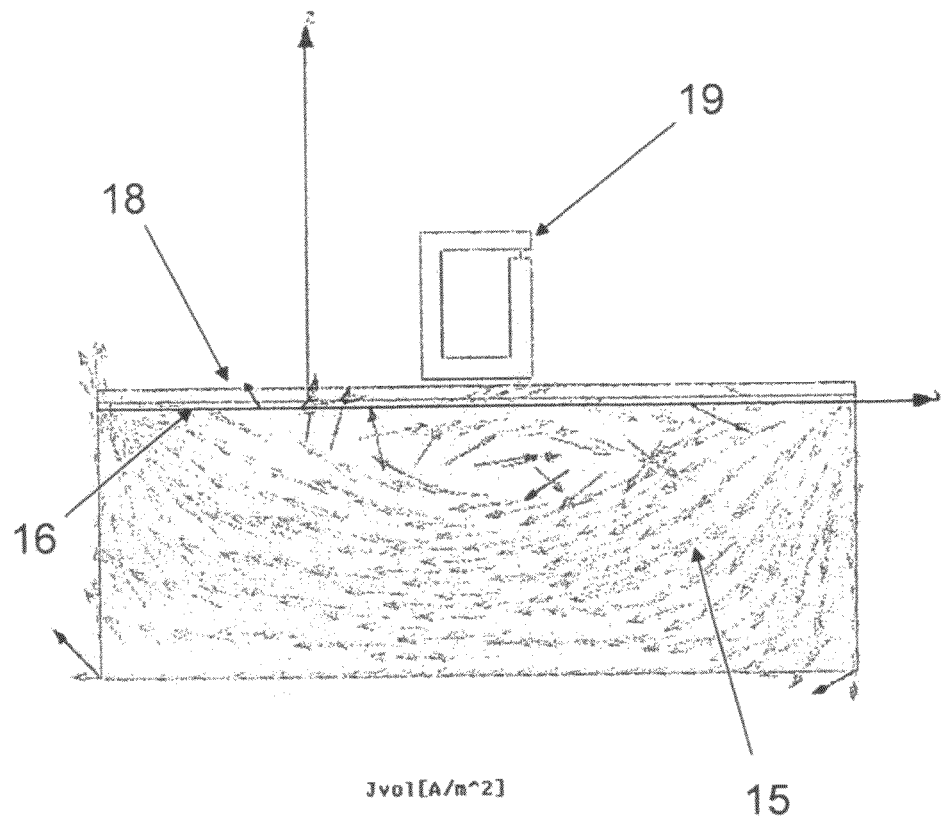
FIG. 15 shows a current vector map in one internal plane of a tissue when the tissue is exposed to a primary magnetic field as disclosed herein.
Figure 16:
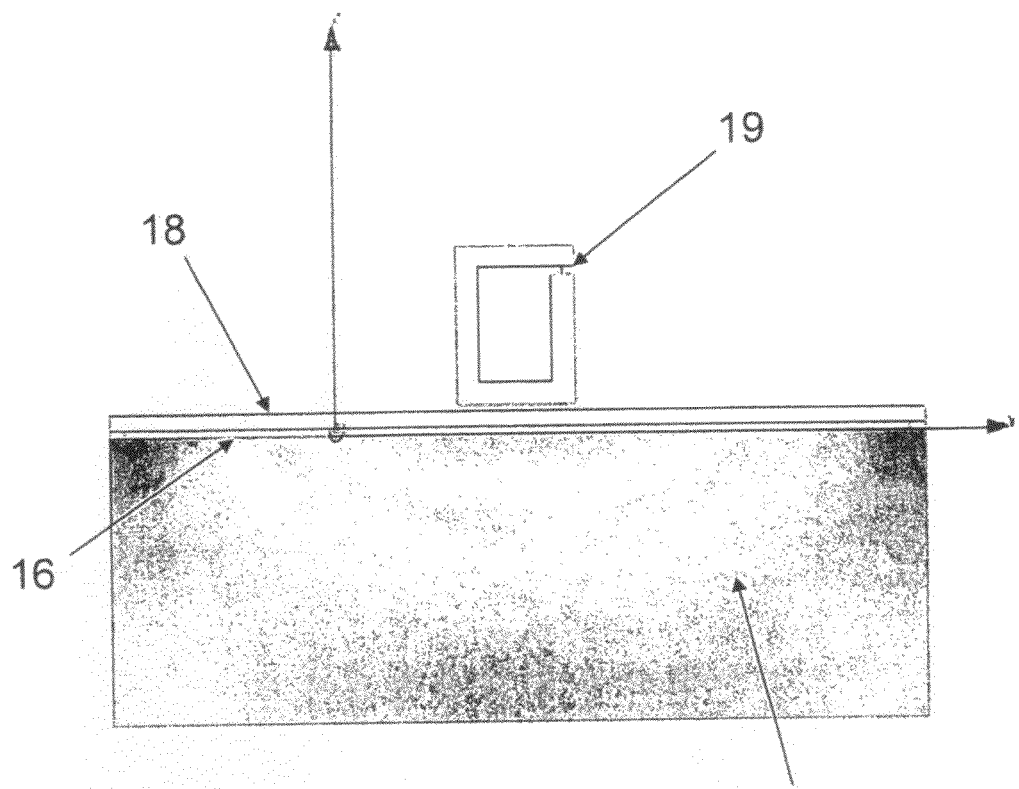
FIG. 16 shows a current density map in one internal plane of a tissue when the tissue is exposed to a primary magnetic field as disclosed herein.

A computer simulations was performed to provide an illustration of the operation of an electrosurgical device employing a primary magnetic field. A current vector map is shown in FIG. 15. Target region 15 provided a model for a treatment tissue such as skin. Conducting element 18 contacted target surface 16. A primary magnetic field was generated by inductive element 19. The electrical current density field is shown within the target region 15 as a series of arrows. FIG. 16 shows a current density map for the simulation.

It can be seen from the simulation data that the current density near target surface 16 is lower than the current density in tissue that is farther from the surface. This shows that the primary magnetic field supplied by inductive element 19 is effective in producing current in deeper layers in the target tissue, while conducting element 18 is effective is minimizing the current density near the treatment surface.

What is claimed is:
1. A method for treating a biological tissue, the method comprising:
    applying to the tissue an electromagnetic field,
        wherein the tissue has a surface, and
        wherein the electromagnetic field is generated by providing RF power to one or more primary electrodes and is effective to create an electrical current in the tissue at a first depth below the surface and an elec- trical current in the tissue at a second depth below the surface wherein the first depth is closer to the surface than the second depth; and modifying the electromagnetic field with a supplemental magnetic field to make the current at the second depth larger than the current in the first depth, wherein the current at the first depth remains below the level sufficient to cause ablation.

2. The method of claim 1, wherein the supplemental magnetic field is generated by providing electrical current to one or more supplemental electrodes.

3. The method of claim 2, wherein the one or more supplemental electrodes are selected from wires, coils, spirals, rods, magnetic materials, and combinations thereof, and wherein the electrical current is selected from AC and DC.

4. The method of claim 1, further comprising controlling the electrical current within the tissue at either the first depth or the second depth by adjusting at least one parameter of either the electromagnetic field or the supplemental magnetic field with respect to the other, wherein the at least one parameter is selected from magnitude, direction, phase, polarity and frequency.

5. The method of claim 1, wherein the supplemental magnetic field interacts with the electromagnetic field so as to modify the current at the first depth.

6. The method of claim 5, wherein the current at the second depth is sufficient to heat the tissue to a temperature effective to cause contraction of collagen.

7. The method of claim 1, wherein the RF power provided to the one or more primary electrodes has a frequency that is greater than about 800 KHz.

8. The method of claim 1, wherein the total amount of power provided to the tissue from the one or more primary electrodes is sufficient to cause heating of the tissue to a temperature effective to cause contraction of collagen.

9. The method of claim 1, wherein the electromagnetic field and the supplemental magnetic field are configured to increase a tissue temperature below the surface more than the tissue temperature at the surface of the tissue.

10. A device for applying RF energy to biological tissue comprising:

one or more primary electrodes disposed on a treatment probe;

means for supplying RF energy to the one or more primary electrodes; and means for creating a supplemental magnetic field, wherein the primary electrodes and the RF energy supply are configured to create an electrical current in the tissue at a first depth below a tissue surface and an electrical current in the tissue at a second depth below the surface, wherein the first depth is closer to the surface than the second depth, wherein the means for creating the supplemental magnetic field are configured to modify the RF energy supply through the primary electrodes to make the current at the second depth larger than the current in the first depth, and wherein the current at the first depth remains below the level sufficient to cause ablation.

11. The device of claim 10, wherein the means for supplying RF energy to the one or more primary electrodes comprises an RF generator capable of supplying RF energy with a frequency of at least 850 KHz.

12. The device of claim 11, wherein the one or more primary electrodes are configured to create an electromagnetic field in the tissue, and wherein the supplemental magnetic field is capable of modifying the electromagnetic field.

13. The device of claim 12, wherein the means for creating a supplemental magnetic field comprises one or more supplemental electrodes.

14. The device of claim 13, wherein the one or more primary electrodes and the one or more supplemental electrodes are configured such that the electromagnetic field and the supplemental magnetic field interact to modify at least the current at the first depth below the surface of the tissue.

15. The device of claim 10, wherein the device is capable of supplying RF energy to the tissue in an amount sufficient to cause contraction of collagen in the tissue.

16. The device of claim 15, wherein the RF power supplied to the tissue is at least 5 Watts.

17. The device of claim 10, wherein the electrical currents and the supplemental magnetic field are configured to increase a tissue temperature below the surface more than the tissue temperature at the surface of the tissue.

18. A device for applying RF energy to biological tissue comprising:

at least one primary electrode connected to an RF power supply and configured to create, by phase controlled RF technology, an electrical current in the tissue at a first depth below a tissue surface and an electrical current in the tissue at a second depth below the surface, wherein the first depth is closer to the surface than the second depth, and means for creating a supplemental magnetic field which are configured to modify the RF energy supply through the at least one primary electrode to make the current at the second depth larger than the current in the first depth, wherein the current at the first depth remains below the level sufficient to cause ablation.

* * * * *